United States Patent [19]
Ito et al.

[11] Patent Number: 5,837,711
[45] Date of Patent: Nov. 17, 1998

[54] SUBSTITUTED QUINUCLIDINES AS SUBSTANCE P ANTAGONISTS

[75] Inventors: Fumitaka Ito, Chita-gun; Toshihide Kokura, Handa; Masami Nakane, Nagoya; Kunio Satake, Handa; Hiroaki Wakabayashi, Kariya, all of Japan

[73] Assignee: Pfizer Inc., New York, N.Y.

[21] Appl. No.: 428,240

[22] PCT Filed: Sep. 30, 1993

[86] PCT No.: PCT/US93/09169

§ 371 Date: Apr. 28, 1995

§ 102(e) Date: Apr. 28, 1995

[87] PCT Pub. No.: WO94/10170

PCT Pub. Date: May 11, 1994

[30] Foreign Application Priority Data

Oct. 28, 1992 [JP] Japan ................................ 4-290569

[51] Int. Cl.$^6$ ...................... C07D 453/02; A61K 31/44
[52] U.S. Cl. ............................. 514/305; 546/133
[58] Field of Search ............... 514/305; 546/133

[56] References Cited

U.S. PATENT DOCUMENTS

| | | | |
|---|---|---|---|
| 4,908,370 | 3/1990 | Naylor et al. | 514/305 |
| 5,242,930 | 9/1993 | Baker et al. | 514/305 |
| 5,273,972 | 12/1993 | Jagdmann et al. | 514/210 |
| 5,451,586 | 9/1995 | Lowe, III | 514/305 |
| 5,538,982 | 7/1996 | Hagan et al. | 514/305 |
| 5,569,662 | 10/1996 | Satake et al. | 514/305 |
| 5,604,241 | 2/1997 | Ito et al. | 514/305 |

FOREIGN PATENT DOCUMENTS

| | | | |
|---|---|---|---|
| WO 90/05729 | 5/1990 | WIPO | 514/305 |
| WO 92/20676 | 11/1992 | WIPO | 514/305 |

Primary Examiner—Matthew V. Grumbling
Attorney, Agent, or Firm—Peter C. Richardson; Paul H. Ginsburg; B. Timothy Creagan

[57] ABSTRACT

Certain novel substituted quinuclidine compounds having the ability to antagonize substance P and having the following formula:

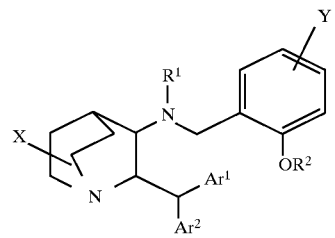

wherein $Ar^1$ and $Ar^2$ are each, independently, thienyl, phenyl, fluorophenyl, chlorophenyl or bromophenyl;

X is $—CONR^3R^4$, $—CO_2R^3$, $—CH_2OR^3$, $—CH_2NR^3R^4$ or $—CONR^3OR^4$;

$R^1$, $R^3$ and $R^4$ are each, independently, hydrogen or alkyl having 1 to 4 carbon atoms;

$R^2$ is alkyl having 1 to 4 carbon atoms;

Y is alkylsulfonyl having 1 to 4 carbon atoms, N-alkyl-N-alkanoylamino (which may be substituted by halogen in the alkanoyl moiety) having 1 to 4 carbon atoms in the alkyl and the alkanoyl moieties, N-alkyl-N-alkylsulfonylamino (which may be substituted by halogen in the alkylsulfonyl moiety) having 1 to 4 carbon atoms in the alkyl and the alkyl sulfonyl moieties, alkenyl having 2 to 4 carbon atoms, alkynyl having 2 to 4 carbon atoms, halosubstituted alkyl having 1 to 4 carbon atoms, alkylamino having 1 to 4 carbon atoms, alkanoylamino (which may be substituted by halogen) having 1 to 4 carbon atoms or alkylsulfonylamino (which may be substituted by halogen) having 1 to 4 carbon atoms.

These compounds are useful in the treatment gastrointestinal or central nervous system disorders and the alleviation of inflammatory diseases, asthma, pain and migraine in mammals and as the active ingredient in pharmaceutical compositions for treating such conditions.

12 Claims, No Drawings

SUBSTITUTED QUINUCLIDINES AS SUBSTANCE P ANTAGONISTS

This application is the United States national phase application of PCT Patent Application PCT/US93/09169, filed Sep. 30, 1993, which was a continuation of Japanese Patent Application 290569/92, filed Oct. 28, 1992.

TECHNICAL FIELD

This invention relates to novel and useful substituted quinuclidine compounds of interest to those in the field of medical chemistry and chemotherapy. More particularly, it is concerned with a novel series of substituted 3-aminoquinuclidines, including their pharmaceutically acceptable salts, which are of special value in view of their ability to antagonize substance P. In this way, these compounds are of use in treating gastrointestinal disorders, central nervous system disorders, inflammatory diseases, asthma, pain and migraine. The invention also includes a new method of therapy within its scope.

BACKGROUND ART

E. J. Warawa in U.S. Pat. No. 3,560,510 discloses certain 3-amino-2-benzhydrylquinuclidines as being useful as diuretic agents, with the corresponding unsubstituted 3-benzylamino compounds acting as intermediates for same. Additionally, E. J. Warawa et al. in the *Journal of Medicinal Chemistry*, Vol.18, p.587 (1975) extends this work to other members of the series wherein the 3-amino moiety is either ethylamino, β-phenylethylamino, β-isopropylamino, or 2-furfurylamino, but in no instance is there any substitution on the phenyl group itself.

Furthermore, neither of the aforementioned documents teaches or suggests any of these compounds to be useful as substance P antagonists.

Substance P is a naturally occurring undecapeptide belonging to the tachykinin family of peptides, the latter being so-named because of their prompt stimulatory action on smooth muscle tissue. More specially, substance P is a pharmaceutically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine (see B. E. B. Sandberg et al., *Journal of Medicinal Chemistry*, Vol. 25, p.1009 (1982)), as well as in central nervous system disorders such as anxiety and schizophrenia, in respiratory and inflammatory diseases such as asthma and rheumatoid arthritis, respectively, and in gastrointestinal disorders and diseases of GI tract, like ulcerative colitis and Crohn's diseases, etc (see D. Regoli in "*Trends in Cluster Headache*" edited by F. Sicuteri et al., Elsevier Scientific Publishers, Amsterdam, 1987, PP. 85–95).

In the recent past, some attempts have been made to provide peptide-like substances that are antagonists for substance P and other tachykinin peptides in order to more effectively treat the various disorders and diseases listed above. The peptide-like nature of such substances makes them too labile from a metabolic point of view to serve as practical therapeutic agents in the treatment of disease. The non-peptidic antagonists of the present invention, on the other hand, do not possess this drawback, being far more stable from a metabolic point of view than the previously-discussed prior art agents.

Compounds of similar structure and similar pharmacological activity to the object compounds of the present invention are described in WO 90/05729 and WO 92/20676.

WO 90/05729 discloses a series of cis-3-[(cyclic) methylamino]-2-[(α-substituted)arylmethyl]quinuclidines including 2-benzhydryl derivatives, 2-substituted benzhydryl derivatives (wherein the substituents were alkyl, alkoxy, halogen and the like), 2-(bis-(2-thienyl)methyl) derivatives and the like.

WO 92/20676 discloses mainly a series of 3-[2-methoxy-5-(substituted)benzylamino]-2-benzhydryl quinuclidines including 4-alkenyl derivatives, 6-phenethyl derivatives, 5- and 6-dialkylaminocarbonyl derivatives, 5-dialkylaminoalkyl derivatives, 6-hydroxyalkyl derivatives, 5-alkylaminocarbonyl derivatives, 5-aminocarbonyl derivatives, 5-carboxyl derivatives, 5- and 6-alkoxycarbonyl derivatives, 5-(N-alkoxy-N-alkyl) aminocarbonyl derivatives, 5-morpholinocarbonyl derivatives and the like. Additionally, the quinuclidine compounds disclosed in WO 92/20676 have various kind of substituents also at 5-position on the benzylamino moiety i.e alkoxy (methoxy), alkyl (isopropyl), alkylthio (methylthio), halo-substituted alkoxy (trifluoromethoxy), halogen, alkylsulfinyl (methylsulfinyl), dialkylamino (dimethylamino) and the like. Further-more, it shows that compounds disclosed in both WO 90/05729 and WO 92/20676 have activity as substance P antagonists, anti-inflammatory activity and anti-psychotic activity.

The present inventors have worked to prepare compounds useful as substance P antagonist, and after extensive research, have succeeded in synthesizing a series of compounds as will be disclosed in detail herein.

BRIEF DISCLOSURE OF THE INVENTION

The present invention provides novel substituted quinuclidine derivatives of the following chemical formula I and its pharmaceutically acceptable salt:

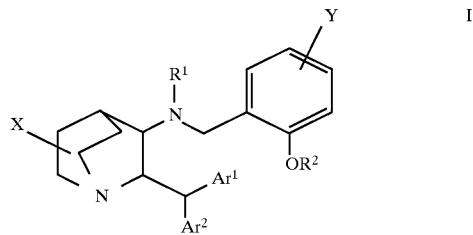

wherein $Ar^1$ and $Ar^2$ are each, independently, thienyl, phenyl, fluorophenyl, chlorohenyl or bromophenyl; X is —$CONR^3R^4$, —$CO_2R^3$, —$CH_2OR^3$, —$CH_2NR^3R^4$ or —$CONR^3OR^4$; $R^1$, $R^3$ and $R^4$ are each, independently, hydrogen or alkyl having 1 to 4 carbon atoms; $R^2$ is alkyl having 1 to 4 carbon atoms; Y is alkylsulfonyl having 1 to 4 carbon atoms, N-alkyl-N-alkanoylamino (which may be substituted by halogen in the alkanoyl moiety) having 1 to 4 carbon atoms in the alkyl and the alkanoyl moieties, N-alkyl-N-alkylsulfonylamino (which may be substituted by halogen in the alkylsulfonyl moiety) having 1 to 4 carbon atoms in the alkyl and the alkyl sulfonyl moieties, alkenyl having 2 to 4 carbon atoms, alkynyl having 2 to 4 carbon atoms, halosubstituted alkyl having 1 to 4 carbon atoms, alkylamino having 1 to 4 carbon atoms, alkanoylamino (which may be substituted by halogen) having 1 to 4 carbon atoms or alkylsulfonyl-amino (which may be substituted by halogen) having 1 to 4 carbon atoms.

The compounds of formula I show pharmaceutical activity as substance P antagonists. Therefore they are useful for treatment or prevention of a condition selected from the group consisting of inflammatory diseases (e.g., arthritis, psoriasis, asthma and inflammatory bowel disease), anxiety, depression or dysthymic disorders, colitis, psychosis, pain, gastroesophageal reflux disease, allergies such as eczema and rhinitis, chronic obstructive airways disease, hypersensitivity disorders such as poison ivy, vasospastic disease such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human.

Accordingly, the present invention includes pharmaceutical compositions for antagonizing mammal's substance P which comprises a pharmaceutically acceptable carrier or diluent and a compound of formula I or a pharmaceutically acceptable salt thereof. These pharmaceutical compositions are useful for treating or preventing one of the aforementioned conditions, in a mammals, including a human.

The present invention also relates to a method of antagonizing substance P in a mammalian subject, which comprises administering to said subject an effective amount of a compound of formula I. In this way, the compounds of formula I are useful for treating or preventing the aforementioned conditions in a mammal, including a human.

DETAILED DISCLOSURE OF THE INVENTION

In this specification:

the term "alkyl" is used herein to mean straight or branched hydrocarbon chain radicals including, but not limited to, methyl, ethyl, n-propyl, isopropyl, n-butyl, isobutyl, t-butyl, and the like;

the term "alkenyl" is used herein to mean straight or branched hydrocarbon chain radicals having one double bond including, but not limited to, ethenyl, 1- and 2-propenyl, 2-methyl-1-propenyl, 1- and 2-butenyl and the like;

the term "alkynyl" is used herein to mean straight or branched hydrocarbon chain radicals having one triple bond including, but not limited to, ethynyl, propynyl, butynyl and the like;

the term "halosubstituted alkyl" refers to an alkyl radical substituted with one or more halogens including, but not limited to, chloromethyl, bromoethyl, trifluoromethyl and the like;

the term "alkylsulfonyl" is used herein to mean —$SO_2R^5$ ($R^5$ is alkyl) including, but not limited to, methylsulfonyl, ethylsulfonyl, n-propylsulfonyl, isopropylsulfonyl, n-butyl sulfonyl, isobutylsulfonyl, t-butylsulfonyl and the like;

the term "alkylamino" is used herein to mean —$NHR^6$ ($R^6$ is alkyl) including, but not limited to, methylamino, ethylamino, n-propylamino, isopropylamino, n-butylamino, t-butylamino and the like;

the term "alkanoylamino" is used herein to mean —$NHCOR^7$ ($R^7$ is alkyl or halosubstituted alkyl) including, but not limited to, formylamino, acetylamino, propionylamino, butyrylamino, isobutyrylamino, trifluoroacetylamino and the like;

the term "alkylsulfonylamino" is used herein to mean —$NHSO_2R^8$ ($R^8$ is alkyl or halosubstituted alkyl) including, but not limited to, methylsulfonylamino, ethylsulfonylamino, trifluoromethylsulfonylamino and the like;

the term "N-alkyl-N-alkylsulfonylamino" is used herein to mean —$N(R^9)SO_2R^{10}$ ($R^9$ is alkyl and $R^{10}$ is alkyl or halosubstituted alkyl) including, but not limited to, N-methyl-N-methylsulfonylamino, N-ethyl-N-methylsulfonylamino, N-n-propyl-N-methylsulfonylamino, N-isopropyl-N-methyl sulfonylamino, N-methyl-N-trifluoromethylsulfonylamino, N-ethyl-N-trifluoromethylsulfonylamino, N-n-propyl-N-trilfluoromethylsulfonylamino, N-isopropyl-N-trifluoromethyl sulfonylamino; and the term "N-alkyl-N-alkanoylamino" is used herein to mean —$N(R^{11})COR^{12}$ ($R^{11}$ is alkyl and $R^{12}$ is alkyl or halosubstituted alkyl) including, but not limited to, N-acetyl-N-methylamino, N-acetyl-N-ethylamino, N-acetyl-N-n-propylamino, N-acetyl-N-isopropylamino, N-trifluoroacetyl-N-methylamino, N-trifluoroacetyl-N-ethylamino, N-trifluoro-acetyl-N-n-propylamino, N-trifluoroacetyl-N-isopropylamino.

The preferred group for $Ar^1$ and $Ar^2$ is phenyl—i.e., the preferred group for $Ar^1$—CH—$Ar^2$ is diphenylmethyl.

A particularly preferred sub-group of compounds of this invention consists of the compounds of formula 1, wherein $Ar^1$ and $Ar^2$ are each phenyl, $R^1$ is hydrogen, $R^2$ is methyl, X is at the 3-position of the quinuclidine ring and X is either carboxy or aminocarbonyl. Within this particularly preferred sub-group, especially preferred compounds are: (i) compounds in which Y is alkenyl, especially isopropenyl; and (ii) compounds in which Y is methylsulfonyl, N-acetyl-N-methylamino or N-methyl-N-methylsulfonylamino.

Preferred individual compounds of this invention are the following:

(3R,4S ,5S ,6S)-5-(5-isopropenyl-2-methoxybenzylamino)-6-diphenylmethyl-1-azabicyclo[2.2.2]octane-3-carboxamide and 3-carboxylic acid derivative;

(3R,4S,5S,6S)-6-Diphenylmethyl-5-(2-methoxy-5-methylsulfonylbenzylamino)-1-aza-bicyclo[2.2.2]octane-3-carboxamide and 3-carboxylic acid derivative;

(3R,4S,5S,6S)-5-[5-(N-Acetyl-N-methylamino)-2-methoxybenzylamino]-6-diphenyl-methyl-1-azabicyclo[2.2.2]octane-3-carboxamide and 3-carboxylic acid derivative; and (3R,4S,5S,6S)-6-Diphenylmethyl-5-[2-methoxy-5-(N-methyl-N-methylsulfonylamino)-benzylamino]-1-azabicyclo[2.2.2]octane-3-carboxamide and 3-carboxylic acid derivative.

The compounds of the above formula may form acid salts. The pharmaceutically acceptable acid salts are those formed from acids which form non-toxic acid salts.

The novel compounds of the present invention can be prepared by the following methods. The compounds of formula I may be prepared by a number of synthetic methods well known by those skilled in the art. See, for instance, WO 92/120676. Thus, typically, the methods in the following scheme can be employed to prepare the objective compounds of the present invention.

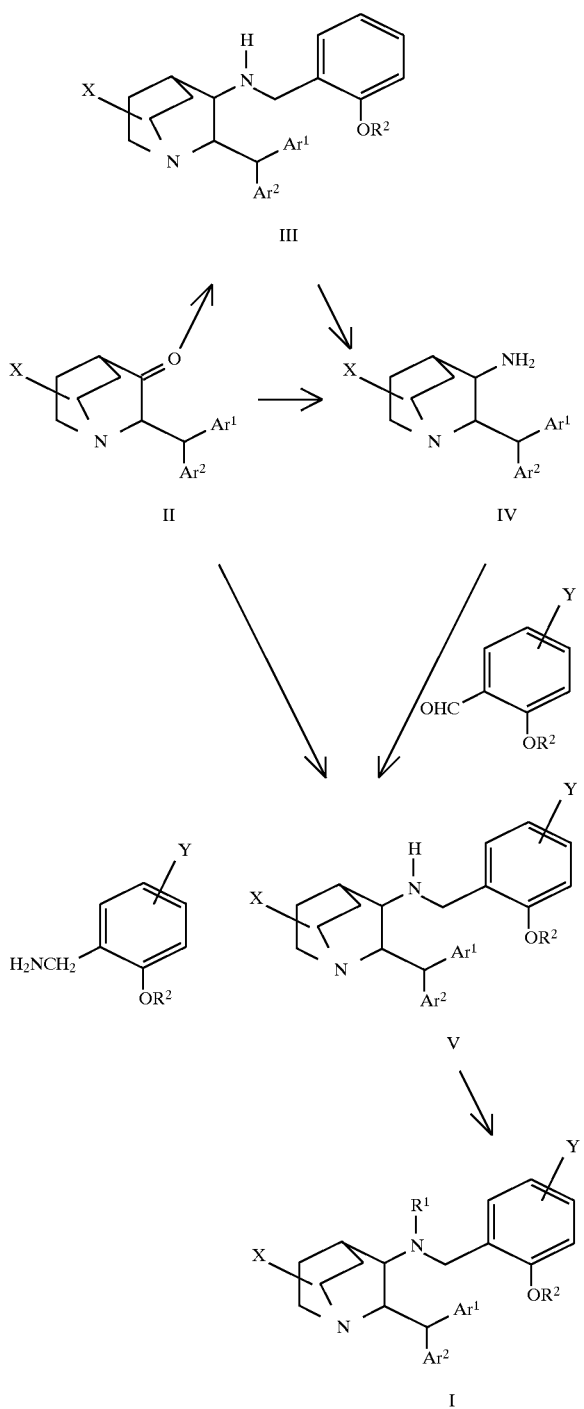

(wherein all the symbols are the same as in formula I).

1st STEP [compound II to IV]:

The first step is through the introduction of a substituted benzylamine (e.g. 2-alkoxy benzylamine etc.) into 3-position of 2-diarylmethyl quinuclidin-3-one II and the subsequent release of the benzyl group from 3-benzylaminoquinuclidine III by using hydrogenation etc. to afford a requisite intermediate, 2-diarylmethylquinuclidin-3-amine IV.

The 2-diarylmethylquinuclidin-3-one II can be synthesized according to the similar manner with methods including prior aryliden-formation and subsequent 1,4-addition reaction described in WO 92/20676. The compound II can be converted to the compound III according to the procedure including reductive amination with a substituted benzylamine well described in WO 92/20676.

The subsequent conversion of the compound III to the compound IV involves reduction by catalytic hydrogenation (i.e. Pearlman's catalyst etc.) or using hydride reagents such as aluminum-based reagents, boranes, borohydrides or trialkylsilanes. In most of the cases, catalytic hydrogenation can be carried out in a suitable organic solvent under hydrogen atmosphere at room temperature for a few hours to a few days, in the presence of a catalyst.

2nd STEP [compound IV to V]:

The second step is through the condensation of 3-amino-2-diarylmethyl-quinuclidine IV and a substituted benzaldehyde followed by reduction. In this second step, the direct arylmethylation can be carried out by the reductive amination [e.g. sodium cyanoborohydride in methanol; *Journal of American Chemical Society*, 93, 2897 (1971)] to the objective compound V. Several other reducing reagents such as $NaBH_4$, $NaBH(OAc)_3$ or trialkylsilanes can be also used to perform this transformation.

Alternatively, the reductive amination of compound II with a corresponding substituted benzylamine can be also employed in order to obtain the objective compound V (see WO 92/20676).

In case of preparing the substituted benzaldehyde, the standard methods (formylation of a substituted alkoxybenzene) well known by those skilled in the art in the following literature can be used: (A) Duff's reaction (hexamethylenetetramine/TFA), *Synthetic Communication*, 15, 61 (1985), (B) $TiCl_4$/dichloromethylether, *Journal of Organic Chemistry*, 51, 4073 (1986), (C) A process by two step reaction (HCl, HCHO, then 2-nitropropane, NaOMe), JP-58-501127 and (D) *Journal of the American Chemical Society*, 2466, (1955).

Additionally, in order to prepare the alkoxybenzaldehyde wherein substituents are alkenyl or alkynyl, a Pd-catalyzed coupling reaction with halosubstituted alkoxybenzene as described in the following literature can be employed: (E) *Angewandte Chemie* International Edition in English, 25, 508 (1986) by J. K. Stille et al., (F) *Journal of Organic Chemistry*, 53, 1170 (1988) by J. K. Stille et al., (G) *Tetrahedron Letters*, 4467 (1975) by K. Sonogashira et al., (H) *Synthesis*, 627 (1980) by N. Hagihara et al..

For example, corresponding alkenyltin compounds or alkynyltin compounds are reacted with 5-halogen-o-anisaldehyde in a reaction inert solvent in the presence of a suitable palladium catalyst. In this reaction, preferred palladium catalysts are $Pd(PPh_3)_4$ or $PdCl_2(PPh_3)_2$. Reaction temperature is usually in the temperature range of room temperature through reflux temperature and the reaction is usually completed within 1 hr to 48 hr. In order to obtain 5-alkenyl-2-alkoxybenzaldehyde, preferred solvents are DMF, THF, toluene and the like. In order to obtain 5-alkynyl-2-alkoxy-benzaldehyde, preferred solvents are diethylamine, piperidine, triethylamine and the like.

In addition, in case of alkylsulfonyl for Y in the above formula, 5-halogen-o-anisaldehyde can be used as a starting compound. First, the 5-position of the starting compound is converted into 5-alkylthio, and then into 5-alkylsulfonyl to afford the objective intermediate, 5-alkylsulfonyl-o-anisaldehyde. Cyclic acetalization is required in the reaction route in order to protect aldehyde group In the above anisaldehyde. The said 5-alkylthio intermediate can be also synthesized by a method described in *Bulletin of the Chemical Society of Japan*, 51, 2435 (1978) by M. Ando et al..

Furthermore, in case of halosubstituted alkyl for Y in the above formula, 4-(halosubstituted alkyl)phenol can be used as a starting compound. The starting compound is alkylated with alkyl halide in the presence of a suitable base. Subsequently, the resulting alkoxybenzene is formylated by a standard method to afford the objective intermediate, 5-halosubstituted alkyl-o-anisaldehyde.

Additionally, in case of alkylamino for Y in the above formula, 3-(1,3-dioxolan-2-yl)4-methoxyaniline can be used as a starting compound. The starting compound is reacted with a corresponding aldehyde in the presence of a suitable reducing agent (i.e. $NaCNBH_4$ etc.) by a method of reductive alkylation to give the objective intermediate, 5-alkylamino-o-anisaldehyde. This procedure is well described in *Journal of the American Chemical Society*, 2897 (1971) by R. F. Borch et al..

In case of N-alkyl-N-alkylsulfonylamino, N-alkyl-N-alkanoylamino, alkanoyl-amino or alkylsulfonylamino for Y in the above formula, 5-nitrosalicylaldehyde can be used as a starting compound. First, the hydroxyl group in 5-nitro salicylaldehyde is alkylated with a suitable alkylating agent (e.g. methyl iodide etc.). Subsequently, after the aldehyde group in the above 5-nitroaldehyde is cyclic-acetalized with a suitable acid catalyst (i.e. camphor sulfonic acid (CSA), p-toluene sulfonic acid etc.), the nitro group in the 5-nitro derivative is converted into an amino group with a suitable catalyst such as $PtO_2$. The amino group in the 5-amino derivative is converted into the respective corresponding functional groups to afford the objective substituted aldehyde. The methods of alkylation, acylation and alkylsulfonyl formation employed in that conversion are the methods well known by those skilled in the art. These methods are described in detail in the following examples.

As mentioned above, synthetic methods for the alkoxy benzaldehyde intermediates wherein Y is substituted at 5-position on 2-alkoxybenzaldehyde and $R^2$ is methyl are mainly described. However, it is a matter of course that the similar methods can be applicable also to the intermediates wherein Y is substituted at other position on 2-alkoxy benzaldehyde or $R^2$ is alkyl groups other than methyl such as ethyl, n-propyl, isopropyl, n-butyl, isobutyl, t-butyl and the like.

As described in WO 92/20676, a substituent group in compound V can be converted to various different substituent groups. For example, a compound having carboxyl, methoxycarbonyl, hydroxymethyl, alkylaminomethyl or dialkylamino-methyl as X can be synthesized from the corresponding carboxamide derivative by methods well known to those skilled in the art.

Additionally, several other carboxamide derivatives, such as those in which X is morpholinocarbonyl, thiamorpholinocarbonyl, N-methyl-N-methoxyaminocarbonyl, N-ethyl-carboxamide, can be synthesized from the corresponding carboxylic acid or carboxamide by utilizing the process documented in WO 92/20676.

In addition, the substituted quinuclidine of the present invention wherein $R^1$ is alkyl can be synthesized by the reductive alkylation (well described in *Journal of the American Chemical Society*, 2897 (1971) by R. F. Borch et al.) of the substituted quinuclidine V, wherein $R^1$ is hydrogen, prepared by the above mentioned methods. Particularly, it can be synthesized by reacting compound V with an aldehyde having corresponding carbon atoms in acetic acid/methanol in the presence of a suitable reducing agent such as $NaCNBH_3$.

Additionally, (+)-(3R,4R)- and (−)-(3S,4S)-N,N-diethyl-5-oxo-1-azabicyclo-[2.2.2]octane-3-carboxamide (see WO 92/20676) are useful for preparing single isomers of the compounds of formula I.

The compounds of formula I can be isolated and purified by conventional rocedures, such as recrystallisation or chromatographic purification.

Inasmuch as the quinuclidine compounds of this invention all possess at least four asymmetric center, they are capable of occurring in various stereoisomeric forms or configurations. The present invention is meant to include all such forms within its scope. For instance, diastereomeric mixtures can be separated by methods well known to those skilled in the art, e.g., by fractional crystallization, column chromatography and the like. Individual diastereomers can also be synthesized by resolving racemic mixtures of formula I using standard procedures of organic chemistry.

Insofar as the quinuclidine compounds of this invention are basic compounds, they are all capable of forming a wide variety of different salts with various inorganic and organic acids. Although such salts must be pharmaceutically acceptable for administration to animals, it is often desirable in practice to initially isolate the quinuclidine base compound from the reaction mixture as a pharmaceutically unacceptable salt and then simply convert to the free base compound by treatment with an alkaline reagent and thereafter, subsequently convert the free base to a pharmaceutically acceptable acid addition salt. The acid addition salts of the quinuclidine base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained.

The acids which are used to prepare the pharmaceutically acceptable acid addition salts of the quinuclidine base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methane sulfonate, ethanesulfonate, benzenesulfonate, p-toluene sulfonate and pamoate [i.e., 1,1'-methylene-bis-(2-hydroxy-3-naphthoate)] salts.

Some quinuclidine compounds of the invention which have also acidic groups are capable of forming base salts with various pharmaceutically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic quinuclidine derivatives. These particular non-toxic base salts include those derived form such pharmaceutically acceptable cations as sodium, potassium, calcium and magnesium, etc. These salts can easily be prepared by treating the aforementioned acidic quinuclidine compounds with an aqueous solution containing the desired pharmaceutically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The quinuclidine compounds of the present invention exhibit significant substance P receptor-binding activity and therefore, are of value in the treatment of a wide variety of clinical conditions which are characterized by the presence of an excess of said substance P activity. Such conditions include gastrointestinal disorders such as ulcer and colitis and other like diseases of the gastrointestinal tract, central nervous system disorders such as anxiety and psychosis, inflammatory diseases such as rheumatoid arthritis and inflammatory bowel diseases, respiratory diseases such as asthma, as well as pain in any of the aforesaid conditions, including migraine. Hence, these compounds are readily adapted to therapeutic use as substance P antagonists for the control and/or treatment of any of the aforesaid clinical conditions in mammals, including humans.

Compounds of the present invention, when tested as an antiinflammatory agent, exhibit a significant degree of activity in the mustard oil-induced rat foot edema test [described by F. Lembeck et al., British Journal of Pharmacology, Vol.105, P.527 (1992)] and the capsaicin-induced plasma extravasation test in guinea pig ureter [described by A. Nagahisa et al., *European Journal of Pharmacology*, Vol.217, P.191 (1992)].

The radiolabelled quinuclidine compounds of the above formula are useful as research and diagnostic tools in metabolism pharmacokinetic studies and in binding assays with the drug in both animal and human. Specific applications in research include radioligand binding assays, autoradiography studies and in vivo binding studies, while specific applications in the diagnostic area include studies of substance P receptor in the human brain, such as up/down regulation in a diseases state, and in vivo binding in the relevant tissues for Inflammation, e.g., immune-type cell or cells that are directly involved in inflammatory bowel disorders and the like. Specifically, the radiolabelled forms of the quinuclidine compounds are the tritium and $^{14}$C-isotopes of the substituted quinuclidine in this invention.

The quinuclidine compounds of formula I can be administered to a mammalian subject, e.g., a human subject, via either the oral, parenteral or topical routes. In general, these compounds are most desirably administered to a human subject in doses ranging from about 1 to 300 mg per day, although variations will necessarily occur depending upon the weight and condition of the subject being treated and the particular route of administration chosen. However, a dosage level that is in the range of about 0.06 mg to about 6 mg per kg of body weight per day is most desirably employed. Variations will occur depending upon the potency of the compound administered and the individual response to said medicament, as well as the severity of the condition being treated and the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

The compounds of the present invention may be administered alone or in combination with pharmaceutically acceptable carriers or diluents by either of the three routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging about 5.0% to about 70% by weight.

For oral administration, tablets containing various excipients such as micro-crystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH )8) if necessary and the liquid diluent first rendered isotonic. These aqueous solutions are suitable for intravenous injection purposes. The oily solutions are suitable for intraarticular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention, as substance P antagonists, is determined by their ability to inhibit the binding of substance P at its receptor sites in bovine caudate tissue or IM-9 cells employing radioactive ligands. The substance P antagonist activity of the herein described quinuclidine compounds is evaluated by using the standard assay procedure described by M. A. Cascieri et al., as reported in *Journal of Biological Chemistry*, Vol.258, p.5158 (1983). This method essentially involves determining the concentration of the individual compound required to reduce by 50% the amount of radiolabelled substance P ligands at their receptor sites in said isolated cow tissues or IM-9 cells, thereby affording characteristic IC$_{50}$ values for each compound tested. In this test, some preferred compounds indicated low IC$_{50}$ values of in the range of 0.1 to 1.9 nM, with respect to inhibition of binding at its receptor.

The anti-inflammatory activity of the compounds of the present invention is demonstrated in the previously mentioned mustard oil-induced rat foot edema test. In this test, anti-inflammatory activity is determined as the percent inhibition of plasma protein extravasation in the hind paw of female Sprague-Dawley rats (weighing 100–150 g) in response to the application of mustard oil to the dorsal skin.

The compounds of the present invention are dissolved in 0.1% methyl cellulose/water and dosed orally 1 h before mustard oil challenge. After Evans Blue injection solution (50 mg/kg, dissolved in saline including 0.02% bovine serum albumin) is injected intravenously, rat's hind paw is painted with 5% mustard oil in paraffin oil and 20 min later the foot is amputated, frozen, pulverized and the Evans Blue dye is extracted and determined colorimetrically.

Alternatively, the antiinflammatory activity of the compounds of the present invention is demonstrated by a capsaicin-induced plasma extravasation test. In this test, antiinflammatory activity is determined as the percent inhibition of plasma protein extravasation in the ureter of male Hartley guinea pigs (weighing 450–600 g) in response to the intraperitoneal injection of capsaicin into anesthetized animals. The compounds of the present invention are dissolved in 0.1% methyl cellulose/water and dosed orally 1 h before capsaicin challenge. Evans Blue dye (30 mg/kg) is administered intravenously 5 min before capsaicin challenge. The animals are killed 10 min after capsaicin injection and both right and left ureters are removed. The Evans Blue dye is extracted and determined calorimetrically.

In the mustard oil-induced rat foot edema test and capsaicin-induced plasma extravasation test, compounds are considered active if the difference in response between the drug-treated animals and a control group receiving the vehicle alone is statistically significant. In those test, some preferred compounds indicated high percentage with respect to inhibition of plasma protein extravasation.

The anti-psychotic activity of the compounds of the present invention as neuroleptic agents for the control of various psychotic disorders is determined primarily by a study of their ability to suppress substance P-induced hypermotility in rats. This study is carried out by first dosing the rats with a control compound or with an appropriate test compound of the present invention, then injecting the rats with substance P by intra-cerebral administration via canula and thereafter measuring their individual locomotor response to said stimuli.

EXAMPLES

The present invention is illustrated by the following examples. However, it should be understood that the invention is not limited to the specific details of these examples. Proton nuclear magnetic resonance spectra (NMR) were measured in $CDCl_3$ at 270 MHz unless otherwise indicated and peak positions are expressed in parts per million (ppm) downfield from tetramethylsilane. The peak shapes are denoted as follows: s, singlet; d, doublet; t, triplet; m, multiplet; br, broad.

Example 1

(3R,4S,5S,6S)-6-Diphenylmethyl-5-(2-methoxy-5-methylsulfonylbenzylamino)-1-aza-bicyclo[2.2.2]octane-3-carboxamide dihydrochloride Synthesis of 5-methylsulfonyl-o-anisaldehyde A solution of 5-bromo-o-anisaldehyde (49.7 g, 231 mmol), ethylene glycol (17.2 g, 277 mmol) and p-toluene sulfonic acid (4.3 g, 23 mmol) in dry toluene (400 ml) was heated at reflux for 21 hr. And then ethylene glycol (4.3 g, 70 mmol) was added to the reaction mixture and heated at reflux for 6 hr. The resulting solution was washed with sat. $NaHCO_3$, water and brine, dried over $MgSO_4$ and concentrated in vacuo to give crude 2-(5-bromo-2-methoxyphenyl)-1,3-dioxolane (75.7 g) as a dark red oil. The residue was added $NaHCO_3$ and then distilled to give 2-(5-bromo-2-methoxyphenyl)-1,3-dioxolane (52.8 g, 88.3%) as a colorless oil.

$^1$H NMR ($CDCl_3$) δ: 7.64 (d, J=2.6 Hz, 1H), 7.42 (dd, J=2.6, 8.8 Hz, 1H), 6.78 (d, J=8.8 Hz, 1H), 6.10 (s, 1H), 4.16–4.00 (m, 4H), 3.85 (s, 3H).

To a stirred cooled (−78° C.) solution of 2-(5-bromo-2-methoxyphenyl)-1,3-dioxolane (51.13 g, 197.3 mmol) in THF (300 ml) was added dropwise a 1.6M-n-butyl lithium (185 ml,296 mmol) under $N_2$ atmosphere. And the mixture was stirred at −78° C. for 2.5 hr. To the reaction mixture was added dropwise dimethyl disuffide (23.1 ml, 256.5 mmol) at the same temperature. The reaction mixture was stirred at −78° C. for 1 hr and then quenched with water. After removal of the solvent, the residue was extracted with $CH_2Cl_2$. The organic layer was washed with water and brine, dried over $MgSO_4$ and concentrated in vacuo. The resulting residue was purified by chromatograph on silica gel to give 2-(5-methylthio-2-methoxyphenyl)-1,3-dioxolane (34.45 g, 77.2%).

$^1$H NMR ($CDCl_3$) δ: 7.53 (d, J=2.6 Hz, 1H), 7.30 (dd, J=8.4, 2.6 Hz, 1H), 6.85 (d, J=8.4 Hz, 1H), 6.12 (s, 1H), 4.17–4.00 (m, 4H), 3.85 (s, 3H), 2.45 (s, 3H).

The solution of 2-(5-methylthio-2-methoxyphenyl)-1,3-dioxolane (34.45 g, 152.24 mmol) in 1N-HCl (35 ml)/acetone (700 ml) was stirred at room temperature for 3 hr. After removal of the solvent, water was added to the residue and the mixture was extracted with $CH_2Cl_2$. The combined organic layer was washed with sat. $NaHCO_3$ and brine, dried over $MgSO_4$, concentrated in vacuo and distilled to give 5-methylthio-o-anisaldehyde (24.1 g, 86.7%) as a yellow oil.

$^1$H NMR ($CDCl_3$) δ: 10.4 (s, 1H), 7.72 (d, J=2.6 Hz, 1H), 7.48 (dd, J=8.8, 2.6 Hz, 1H), 6.94 (d, J=8.8 Hz, 1H), 3.91 (s, 3H), 2.46 (s, 3H).

To the mixture of 5-methylthio-o-anisaldehyde (3.0 g, 16.5 mmol) in acetone (30 ml) and water (15 ml) was added 4-methylmorpholine-N-oxide (85.8 g, 49.5 mmol) and 0.18M-osmium tetraoxide aqueous solution (0.95 ml, 0.17 mmol) at room temperature and was allowed to stir for 6 hr. The mixture was quenched by addition of aqueous sodium bisulfite (10 ml). After extraction of the quenched reaction mixture with $CH_2Cl_2$, the combined organic layer was washed with 1N-sodium bisulfate and brine, dried over $MgSO_4$, filtered and concentrated in vacuo. Flash silica gel chromatography of the residue provide 5-methylsulfonyl-o-anisaldehyde (440 mg) as a colorless solid.

$^1$H NMR ($CDCl_3$) δ: 10.46 (s, 1H), 8.38 (d, J=2.6 Hz, 1H), 8.13 (dd, J=8.8, 2.6 Hz, 1H), 7.18 (d, J=8.8 Hz, 1H), 4.06 (s, 3H), 3.07 (s, 3H).

Synthesis of (3R,4S,5S,6S)-6-Diphenylmethyl-5-(-2-methoxy-5-methylsulfonylbenzyl-amino)-1-azabicyclo[2.2.2]octane-3-carboxamide dihydrochloride A mixture of 5-methylsulfonyl-o-anisaldehyde (364 mg,1.7 mmol), (3R,4S,5S,6S)-5-amino-6-diphenylmethyl-1-azabicyclo[2.2.2]octane-3-carboxamide (500 mg, 1.50 mmol) and $NaBH(OAc)_3$ (636 mg, 3.0 mmol) in $CH_2Cl_2$ (10 ml) was stirred at room temperature for 3 hr. The reaction mixture was extracted with $CH_2Cl_2$ (300 ml), washed with $NaHCO_3$ aqueous solution and brine, dried over $MgSO_4$ and concentrated in vacuo. The residue was purified by silica gel chromatography. The resulted product was diluted with HCl/methanol (15 ml), stirred for 30 min and the white precipitate (appeared during the reaction) was collected by filtration to afford a titled compound (589 mg, 58.2%) as a white crystalline.

m.p.: 205°–208° C. (decomp.)

IR (KBr): 3045, 3020, 1685, 1605, 1495, 1455, 1320, 1260, 1130, 1020, 980, 765, 715 $cm^{-1}$.

$^1$H NMR ($CDCl_{31}$ free amine) δ: 7.81 (dd, J=2.6, 8.8 Hz, 1H), 7.54 (d, J=2.6 Hz, 1H), 7.31–7.07 (m, 10H), 6.82 (d, J=8.8 Hz, 1H), 5.73 (br. s, 1H), 5.40 (br. s,1H), 4.46 (d, J=12.1 Hz, 1H), 3.77 (d, J=13.6 Hz, 1H), 3.65–3.61 (m, 1H), 3.57 (s, 3H), 3.27 (d, J=13.6 Hz, 1H), 3.20–3.08 (m, 2H), 3.03 (s, 3H), 2.92–2.66 (m, 3H), 2.44–2.37 (m, 2H), 1.76–1.72 (m, 2H), Example 2

(3R,4S,5S,6S)-6-Diphenylmethyl-5-(-2-methoxy-5-methylsulfonyl-benzylamino)-1-azabicyclo[2.2.2]octane-3-carboxylic acid dihydrochloride A solution of (3R,4S,5S,6S)-6-Diphenylmethyl-5-(-2-methoxy-5-methylsulfonyl-benzylamino)-1-azabicyclo[2.2.2]octane-3-carboxamidedihydrochloride (the compound of Example 1, 400 mg) in conc. HCl (10 ml) was warmed up to 90° C. and stirred for 15 hr. After cooling down to room temperature, the mixture was evaporated in vacuo. The residue was recrystallized from EtOAc-MeOH to give a titled compound (268.2 mg, 55.6%) as a white crystalline.

m.p.: 208°–211° C. (decomp.)

IR (Kbr): 3040, 1725, 1605, 1455, 1400, 1360, 1295, 1130, 1020, 965, 760, 710, 620 cm$^{-1}$.

$^1$H NMR (CDCl$_3$, free amine) δ: 7.77 (dd, J=2.1, 8.6 Hz, 1H), 7.48 (d, J=2.1 Hz, 1H), 7.41–7.07 (m, 10H), 6.80 (d, J=8.6 Hz, 1H), 4.49 (d, J=12.1 Hz, 1H), 4.04 (br.t, 1H), 3.60 (s, 3H), 3.01 (s, 3H), 2.56 (m, 2H), 1.87 (m, 2H), 1.60 (m, 2H).

Example 3

(3R,4S,5S,6S)-6-Diphenylmethyl-5-[2-methoxy-5-(N-methyl-N-methylsulfonylamino)benzylamino]-1-azabicyclo[2.2.2]octane-3-carboxamide dihydrochloride Synthesis of 5-(N-methyl-N-methylsulfonylamino)-o-anisaldehyde To a solution of 5-nitrosalicylaldehyde (1.00 g, 6.0 mmol) in DMF (20 ml) was added NaH (246 mg) and methyl iodide (2.56 g, 18 mmol) at 0° C. The mixture was stirred for 8.5 hr at 60° C. After the reaction mixture was extracted with ether, the extract was washed with aqueous NaHCO$_3$, brine and 5%-HCl/aq.NaCl, dried over MgSO$_4$ and concentrated in vacuo to afford 2-methoxy-5-nitrobenzaldehyde (0.95 g, 87.8%) as a yellow needle.

$^1$H NMR (CDCl$_3$) δ: 10.45 (s, 1H), 8.70 (d, J=2.9 Hz, 1H), 8.45 (dd, J=8.8, 2.9 Hz, 1H), 7.14 (d, J=8.8 Hz, 1H), 4.08 (s, 3H).

A solution of 2-methoxy-5-nitrobenzaldehyde (100 g, 550 mmol), ethylene glycol (36.9 ml, 660 mmol) and CSA (5.00 g) was heated at reflux under dehydrating condition for 5 hr. After removal of the solvent, triethylamine (6 ml) was added to the residue and the mixture was recrystallized from first ethyl acetate and from next isopropanol to give 2-(2-methoxy-5-nitrophenyl)-1,3-dioxolane (99.7 g, 80.5%) as a yellow solid.

$^1$H NMR (CDCl$_3$) δ: 8.44 (d, J=2.9 Hz, 1H), 8.26 (dd, J=8.8, 2.9 Hz, 1H), 6.98 (d, J=8.8 Hz, 1H), 6.14 (s, 1H), 4.20–4.03 (m, 4H), 3.97 (s, 3H).

To a solution of 2-(2-methoxy-5-nitrophenyl)-1,3-dioxolane (1.00 g, 4.4 mmol) in methanol (45 ml) was added PtO$_2$ (20 mg) as a catalyst. The resulted mixture was reacted with Parr Shaker (2.2 kg/cm$_2$) for 1.5 hr. After removal of catalyst by filtration, the reaction mixture was evaporated in vacuo to give crude 2-(5-amino-2-methoxyphenyl)-1,3-dioxolane (894.6 mg, 100%) as a brown oil.

$^1$H NMR (CDCl$_3$) δ: 6.92 (d, J=2.9 Hz, 1H), 6.75 (d, J=8.8 Hz, 1H), 6.66 (dd, J=8.8, 2.9 Hz, 1H), 6.09 (s, 1H), 4.16–3.99 (m, 4H), 3.79 (s, 3H), 3.45 (s, 2H).

To a solution of 2-(5-amino-2-methoxyphenyl)-1,3-dioxolane (867 mg, 4.4 mmol) in pyridine (2 ml) was added methanesulfonyl chloride (375 μl, 4.84 mmol) and stirred for 20 hr. To the resulted reaction mixture was added water and aqueous NaHCO$_3$, and then extracted with ether/CH$_2$Cl$_2$. The extract was evaporated in vacuo to give crude 2-(5-methylsulfonylamino-2-methoxyphenyl)-1,3-dioxolane (1.06 g, 88.1%) as a slight brown oil.

$^1$H NMR (CDCl$_3$) δ: 7.39 (d, J=2.9 Hz, 1H), 7.32 (dd, J=8.8, 2.9 Hz, 1H), 6.89 (d, J=8.8 Hz, 1H), 6.62 (s, 1H), 6.11 (s, 1H), 4.18–4.00 (m, 4H), 3.86 (s, 3H), 2.94 (s, 3H).

To a solution of 2-(5-methylsulfonylamino-2-methoxyphenyl)-1,3-dioxolane (8.63 g, 31.6 mmol) in DMF (30 ml) was added NaH (1.51 g, 37.9 mmol) and methyl iodide (2.36 ml, 37.9 mmol) and then stirred at 60° C. for 1 hr. After aqueous ammonium chloride was added to the reaction mixture, the mixture was extracted with ether/CH$_2$Cl$_2$. The extract was dried over MgSO$_4$ and evaporated in vacuo to give crude 2-[5-(N-methyl-N-methylsulfonylamino)-2-methoxyphenyl]-1,3-dioxolane (10.29 g) as a brown oil.

$^1$H NMR (CDCl$_3$) δ: 7.44 (d, J=2.9 Hz, 1H), 7.30 (dd, J=8.8, 2.9 Hz, 1H), 6.84 (d, J=8.8 Hz, 1H), 6.02 (s, 1H), 4.07–3.95 (m, 4H), 3.81 (s, 3H), 3.22 (s, 3H), 2.76 (s, 3H).

A solution of 2-[5-(N-methyl-N-methylsulfonylamino)-2-methoxyphenyl]-1,3-dioxolane (4.0 g, 13.9 mmol) in 1N-HCl (4 ml)/acetone (80 ml) was stirred at room temperature for 2 hr. After removal of the solvent, water was added to the residue and the mixture was extracted with CH$_2$Cl$_2$. The extract was washed with brine, dried over MgSO$_4$ and evaporated in vacuo to give crude 5-(N-5-methyl-N-methylsulfonylamino)-o-anisaldehyde (4.0 g, 118%). The resulted crude compound was recrystallized from ethyl acetate/hexane to give 5-(N-methyl-N-methylsulfonylamino)-o-anisaldehyde (2.64. g, 81%).

$^1$H NMR (CDCl$_3$) δ: 10.44 (s, 1H), 7.75 (d, J=2.6 Hz, 1H), 7.67 (dd, J=8.8, 2.6 Hz, 1H), 7.03 (d, J=8.8 Hz, 1H), 3.96 (s, 3H), 3.31 (s, 3H), 2.84 (s, 3H).

(3R,4S,5S,6S)-6-Diphenylmethyl-5-[2-methoxy-5-(N-methyl-N-methylsulfonylamino)benzylamino]-1-azabicyclo[2.2.2]octane-3-carboxamide dihydrochloride This compound was prepared according to a similar manner with Example 1 from (3R,4S,5S,6S)-5-amino-6-diphenylmethyl-1-azabicyclo [2.2.2]octane-3-carboxamide and 5-(N-methyl-N-methylsulfonylamino)-o-anisaldehyde.

m.p.: 188.3°–189.1° C.

IR (KBr): 3435, 1685, 1678, 1502, 1458, 1331, 1246, 1142, 1022, 962 cm$^{-1}$.

$^1$H NMR (CDCl$_3$, free amine) δ: 7.35–7.05 (m, 12H), 6.64 (d, J=8.8 Hz, 1H), 6.34 (br. s, 1H), 5.26 (br. s, 1H), 4.50 ( d, J=12.1 Hz, 1H), 3.76 ( d, J=13.9 Hz, 1H), 3.7–3.55 (m, 1H), 3.40 (s, 3H), 3.35–3.0 (m, 3H), 3.26 (s, 3H), 2.95–2.8 (m, 2H), 2.89 (s, 3H), 2.8–2.6 (m,1H), 2.5–2.2 (m, 2H), 1.8–1.5 (m, 2H).

Example 4

(3 R ,4S ,5S ,6S)-5-[5-(N-Acetyl-N-methylamino)-2-methoxybenzylamino]-6-diphenyl-methyl-1-azabicyclo[2.2.2]octane-3-carboxamide dihydrochloride Synthesis of 5-(N-acetyl-N-methylamino)-o-anisaldehyde To a solution of 2-(5-amino-2-methoxyphenyl)-1,3-dioxolane (an intermediate for the compound of Example 3, 17.3 g, 88.8 mmol) and triethylamine (27 ml, 195.4 mmol) in $CH_2Cl_2$ (30 ml) was added dropwise acetic anhydride (9.3 ml, 97.7 mmol) and then stirred for 20 hr. To the mixture was added brine and then extracted with $CH_2Cl_2$, dried over $MgSO_4$ and concentrated in vacuo to give 2-(5-acetylamino-2-methoxyphenyl)-1,3-dioxolane (21.3 g, >100%) as a brown solid.

$^1$H NMR (CDCl$_3$) δ: 7.71 (s, 1H), 7.64 (dd, J=8.8, 2.9 Hz, 1H), 7.47 (d, J=2.9 Hz, 1H), 6.84 (d, J=8.8 Hz, 1H), 6.11 (s, 1H), 4.13–3.98 (m, 4H), 3.81 (s, 3H), 2.12 (s, 3H).

A solution of 2-(5-acetylamino-2-methoxyphenyl)-1,3-dioxolane (5.0 g, 21.1 mmol) in DMF (16 ml) was added to a suspension of NaH (1.0 g, 25.3 mmol) in DMF (5 ml) and then the mixture was stirred at room temperature for 10 min. To the mixture was added methyl iodide (3.6 g, 25.3 mmol) and then stirred at room temperature for 1 hr. And to the resulted reaction mixture was added ammonium chloride and then extracted with $CH_2Cl_2$. The extract was washed with water and brine, dried over $Na_2SO_4$ and concentrated in vacuo to give crude 2-[5-(N-acetyl-N-methylamino)-2-methoxyphenyl]-1,3-dioxolane (5.0 g, 94%) as a orange oil.

$^1$H NMR (CDCl$_3$) δ: 7.38 (d, J=2.6 Hz, 1H), 7.15 (dd, J=8.8, 2.6 Hz, 1H), 6.93 (d, J=8.8 Hz, 1H), 6.12 (s, 1H), 4.15–4.00 (m, 4H), 3.90 (s, 3H), 3.23 (s, 3H), 1.93 (s, 3H).

A solution of 2-[5-(N-acetyl-N-methylamino)-2-methoxyphenyl]-1,3-dioxolane (5.0 g) in 1N-HCl (4 ml)/acetone (80 ml) was stirred at room temperature for 1.5 hr. After removal of the solvent, water was added to the residue and the mixture was extracted with CHCl$_3$. The extract was washed with brine, dried over $Na_2SO_4$ and concentrated in vacuo to give a crude titled compound (3.1 g, 75%). The resulted crude product was recrystallized from ethyl acetate/hexane to afford the titled compound (2.18 g, 53%) as a brown solid.

$^1$H NMR (CDCl$_3$) δ: 10.46 (s, 1H), 7.66 (d, J=2.6 Hz, 1H), 7.38 (dd, J=8.8, 2.6 Hz, 1H), 7.05 (d, J=8.8 Hz, 1H), 3.98 (s, 3H), 3.23 (s, 3H), 1.86 (s, 3H).

Synthesis of (3R,4S,5S,6S)-5-[5-(N-acetyl-N-methylamino)- 2-methoxybenzylamino]-6-diphenylmethyl-1-azabicyclo[2.2.2]octane-3-carboxamide dihydrochloride This compound was prepared according to a similar manner with Example 1 from (3R,4S,5S,6S)-5-amino-6-diphenylmethyl-1-azabicyclo [2.2.2]octane-3-carboxamide and 5-(N-acetyl-N-methylamino)-o-anisaldehyde.

m.p. : 195.2°–196.0° C.

IR (Kbr): 3410, 1685, 1679, 1632, 1505, 1455, 1391, 1249, 1023 cm$^{-1}$.

$^1$H NMR (CDCl$_3$, free amine): 7.35–7.05 (m, 10H), 6.96 (dd, J=2.6, 8.8 Hz, 1H), 6.73 (d, J=8.8 Hz, 1H), 6.34 (d, J=2.6 Hz, 1H), 5.54 (br. s,1H), 5.47 (br. s, 1H), 4.46 (d, J=11.7 Hz, 1H), 3.85–3.65 (m, 2H), 3.66 (s, 3H), 3.36 (d, J=11.4 Hz, 1H), 3.30–3.00 (m, 4H), 3.20 (s, 3H), 2.80–2.65 (m,1H), 2.60–2.40 (m, 2H), 1.90–1.60 (m, 2H), 1.81 (s, 3H).

Example 5

(3R,4S,5S,6S)-6-Diphenylmethyl-5-(5-isopropenyl-2-methoxy)benzylamino-1-aza-bicyclo[2.2.2]octane-3-carboxamide Synthesis of 5-isopropenyl-o-anisaldehyde 5-isopropenyl-o-anisaldehyde was prepared by J. K. Stille's method [Journal of Organic Chemistry, 52, 422 (1987)].

Tri-n-butyl-isopropenyltin (12.1 g, 36.6 mmol) dissolved in toluene (10 ml) was added to a mixture of 5-bromo-o-anisaldehyde (6.00 g, 27.9 mmol), tetrakis(triphenylphosphine)palladium (1.21 g, 1.05 mmol), and 2,6-t-butyl4-methylphenol (10 mg) in toluene (50 ml) under nitrogen at room temperature. This mixture was heated at reflux for 7 hr. Ether and aq. KF solution (80 ml) were added to the reaction mixture, and the resulting solution was stirred for 3 hr. Insoluble materials were removed by filtration through Celite. The filtrate was extracted with ether, and the organic phase was washed with 1N-NaHSO$_4$ aq. NaHCO$_3$ and brine. The extracts were dried over $Na_2SO_4$, and concentrated by evaporation. The residual oil was purified by chromatography (SiO$_2$, 140 g, 5%-EtOAc/hexane) to afford 5-isopropenyl-o-anis-aldehyde, as a yellow oil (2.49 g, 51%).

$^1$H NMR (CDCl$_3$) δ: 10.47 (s, 1H), 7.93 (d, J=2.6 Hz, 1H), 7.69 (dd, J=8.8, 2.6 Hz, 1H), 6.96 (d, J=8.8 Hz, 1H), 5.35 (br. s, 1H), 5.07 (m, 1H), 3.94 (s, 3H), 2.15 (m, 3H).

The said tri-n-butyl-isopropenyltin was prepared according to D. Seyferth's method [Journal of American Chemical Society, 79, 515 (1957)].

Synthesis of (3R,4S,5S,6S)-6-Diphenylmethyl-5-(5-isopropenyl-2-methoxy)benzyl-amino-1-azabicyclo [2.2.2] octane-3-carboxamide This compound was prepared according to a similar manner with Example 1 from (3R,4S,5S,6S)-5-amino-6-diphenylmethyl-1-azabicyclo[2.2.2]octane-3-carboxamide and 5-isopropenyl-o-anisaldehyde.

m.p.: 223°–237° C. (decomp.)

IR (nujol): 3300, 3200, 3150, 1685, 1655 cm$^{-1}$.

$^1$H NMR (CDCl$_3$, free amine) δ: 7.35–7.10 (m, 11H), 6.94 (d, J=2.2 Hz, 1H), 6.68 (d, J=8.6 Hz, 1H), 5.37 (br. s, 2H), 5.22 (br. s, 1H), 5.00 (m, 1H), 4.47 (d, J=12.2 Hz, 1H), 3.70–3.53 (m, 2H), 3.56 (s, 3H), 3.55 (d, J=12.0 Hz, 1H), 3.35–2.95 (m, 3H), 3.23 (d, J=12.0 Hz, 1H), 2.66 (brt, J=12.0 Hz, 1H), 2.52–2.40 (m, 2H), 2.10 (d, J=0.50 Hz, 3H), 1.90 –1.80 (m, 1H), 1.60 (m, 1H).

We claim:

1. A compound of the following chemical formula and its pharmaceutically acceptable salt:

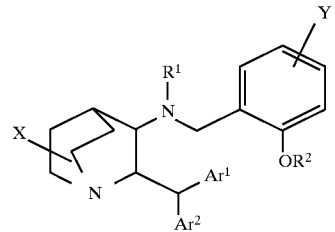

wherein Ar$^1$ and Ar$^2$ are each, independently, thienyl, phenyl, fluorophenyl, chlorophenyl or bromophenyl;

X is —CONR$^3$R$^4$, —CO$_2$R$^3$, —CH$_2$OR$^3$, —CH$_2$NR$^3$R$^4$ or —CONR$^3$OR$^4$;

R$^1$, R$^3$ and R$^4$ are each, independently, hydrogen or alkyl having 1 to 4 carbon atoms;

R$^2$ is alkyl having 1 to 4 carbon atoms;

Y is alkylsulfonyl having 1 to 4 carbon atoms, N-alkyl-N-alkanoylamino (which may be substituted by halogen in the alkanoyl moiety) having 1 to 4 carbon atoms in the alkyl and the alkanoyl moieties, N-alkyl-N-alkylsulfonylamino (which may be substituted by halogen in the alkylsulfonyl moiety) having 1 to 4 carbon atoms in the alkyl and the alkyl sulfonyl moieties, alkenyl having 2 to 4 carbon atoms, alkynyl having 2 to 4 carbon atoms, halosubstituted alkyl having 1 to 4 carbon atoms, alkylamino having 1 to 4 carbon atoms, alkanoylamino (which may be substituted by halogen) having 1 to 4 carbon atoms or alkylsulfonylamino (which may be substituted by halogen) having 1 to 4 carbon atoms.

2. A compound according to claim 1, wherein $Ar^1$ and $Ar^2$ are each phenyl.

3. A compound according to claim 2, wherein $R^2$ is methyl and $R^1$ is hydrogen.

4. A compound according to claim 3, wherein X is at the 3-position of the quinuclidine ring and X is carboxy or aminocarbonyl.

5. A compound according to claim 4, wherein Y is said alkenyl.

6. A compound according to claim 5, wherein Y is isopropenyl.

7. A compound according to claim 4, wherein Y is methylsulfonyl, N-acetyl-N-methylamino or N-methyl-N-methylsulfonylamino.

8. A compound according to claim 1, wherein the compound is selected from:

(3R,4S,5S,6S)-5(5-isopropenyl-2-methoxybenzylamino)-6-diphenylmethyl-1-azabicyclo[2.2.2]octane-3-carboxamide;

(3R,4S ,5S ,6S)-6-Diphenylmethyl-5-(2-methoxy-5-methylsulfonylbenzylamino)-1-azabicyclo[2.2.2]octane-3-carboxamide;

(3R,4S ,5S ,6S)-5-[5-(N-Acetyl-N-methylamino)-2-methoxybenzylamino]-6-diphenylmethyl-1-azabicyclo[2.2.2]octane-3-carboxamide;

(3R,4S,5S,6S)-6-Diphenylmethyl-5-[2-methoxy-5-(N-methyl-N-methylsulfonylamino)benzylamino]-1-azabicyclo[2.2.2]octane-3-carboxamide; and (3R,4S ,5S ,6S)-6-Diphenylmethyl-5-(2-methoxy-5-methylsulfonylbenzylamino)-1-azabicyclo[2.2.2]octane-3-carboxylic acid.

9. A pharmaceutical composition for antagonizing substance P in a mammalian subject which comprises a therapeutically effective amount of a compound of claim 1 or its pharmaceutically acceptable salt together with a pharmaceutically acceptable carrier.

10. A pharmaceutical composition for the treatment of gastrointestinal or central nervous system disorders and the alleviation of inflammatory disease, asthma, pain or migraine in a mammalian subject which comprises a therapeutically effective amount of a compound of claim 1 or its pharmaceutically acceptable salt together with a pharmaceutically acceptable carrier.

11. A method for antagonizing substance P in a mammalian subject, which comprises administering to said subject an effective amount of a compound of claim 1.

12. A method of treating a gastrointestinal or central nervous system disorders, or alleviating an inflammatory disease, asthma, pain or migraine, in a mammalian subject, which comprises administering to said subject a therapeutically effective amount of a compound of claim 1.

* * * * *